United States Patent
Blume

(10) Patent No.: US 6,677,129 B1
(45) Date of Patent: Jan. 13, 2004

(54) METHOD FOR DETECTING HELICOBACTER PYLORI INFECTION

(76) Inventor: Richard S. Blume, 240 Main St., Northport, NY (US) 11768

( * ) Notice: Subject to any disclaimer, the term of this patent is extended or adjusted under 35 U.S.C. 154(b) by 796 days.

(21) Appl. No.: 09/476,822

(22) Filed: Jan. 3, 2000

Related U.S. Application Data

(63) Continuation-in-part of application No. 09/120,405, filed on Jul. 22, 1998, now abandoned.

(51) Int. Cl.$^7$ .................................................. C12Q 1/58
(52) U.S. Cl. .......................................... 435/12; 435/34
(58) Field of Search ............................. 435/18, 28, 29, 435/30, 34, 69.2, 12, 184

(56) References Cited

U.S. PATENT DOCUMENTS

| | | | | |
|---|---|---|---|---|
| 5,542,419 A | * | 8/1996 | Moulton-Barrett et al. | 128/630 |
| 5,719,052 A | * | 2/1998 | Ito et al. | 435/287.1 |
| 5,753,711 A | * | 5/1998 | Schwabe et al. | 514/643 |
| 5,834,002 A | * | 11/1998 | Athanikar | 424/440 |

OTHER PUBLICATIONS

Parsonnet, J. et al., "Fecal and oral shedding of *Helicobacter pylori* from healthy infected adults," *JAMA*, Dec. 15, 1999, 282(23): 2240–2245.

Blume, R., "Detection of urease activity in the pharynx," *Gastroenterology* Apr., 1999, 116(4):A124, Abstract G0535.

* cited by examiner

*Primary Examiner*—Ralph Gitomer

(57) ABSTRACT

A method for oral sampling and rapid, specific detection of the urease activity associated with *H. pylori* infection in humans without the need for sample incubation. The method involves the steps of gargling, or gargling and rinsing the mouth with a measured volume of sampling liquid with known characteristics; retrieving an oral liquid sample 10 into a collection container 12; acidifying the oral liquid sample; and contacting the oral liquid sample within the collection container with a urease detecting pad 14 containing urease substrate for detection of urease activity present in the oral liquid sample. The urease detecting pad can contain pH indicator for visual identification of color change associated with presence of urease activity in the oral liquid sample. The method provides for sampling of both the pharynx and mouth of the human, either separately or combined for diagnosis. pH change of the oral liquid sample associated with placing of the urease detecting pad onto the sample provides an additional or separate indicator of the presence of urease activity in the oral liquid sample.

6 Claims, 1 Drawing Sheet

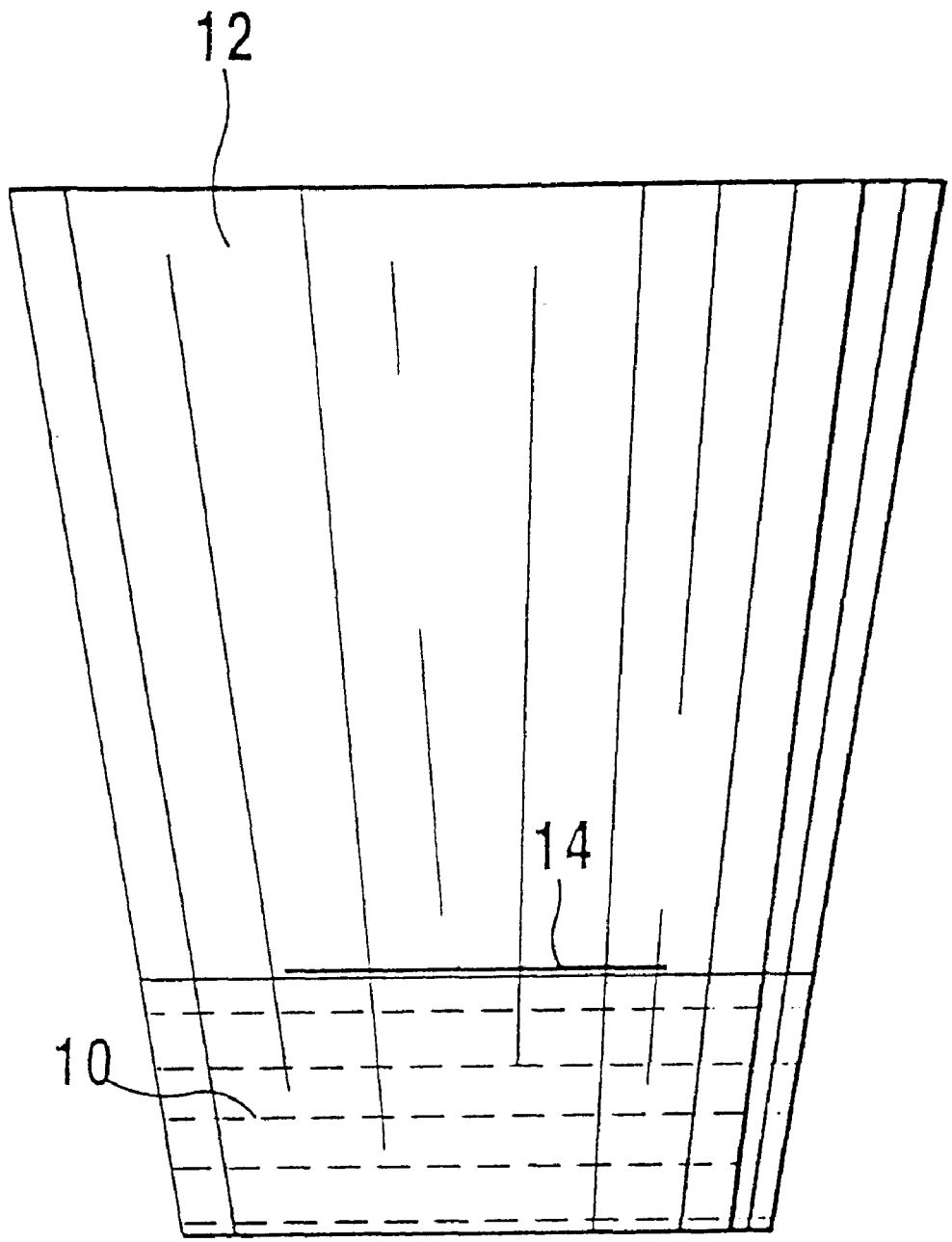
FIG

METHOD FOR DETECTING *HELICOBACTER PYLORI* INFECTION

This is a continuation-in-part of application Ser. No. 09/120,405, Filed Jul. 22, 1998 now abandoned.

BACKGROUND

1. Field of Invention

The present invention relates generally to health care diagnostics and specifically to an improved method for oral sampling in a human subject for rapid detection of the presence of infection, the specific embodiment being the detection of the urease activity associated with *Helicobacter pylori* infection in the human.

*Helicobacter pylori* (*H. pylori*) is a common pathogen in humans and specifically causes disease of the stomach. In industrialized countries, infection can be present in half of all persons older than 50 years. First identified in 1983, *H. pylori* is now known to cause chronic gastritis or inflammation of the stomach, as well as gastric and duodenal ulcers. It is also associated with gastric malignancy (Thomas, E., et al., "The role of the oral cavity in *Helicobacter pylori* infection," Am. J. Gastroenterol., 1997 December; 92(12): 2148–2154). This and other publications cited are incorporated by reference herein.

Combinations of antibiotics and bismuth and/or gastric acid blocking agents are used to treat *H. pylori* infection in the stomach. Bismuth salicylate inhibits the urease activity of *H. pylori* (Prewett, E., et al., "Comparison of one-day oral dosing with three bismuth compounds for the suppression of *Helicobacter pylori* assessed by the 13C-urea breath test," Aliment. Pharmacol. Ther., 1992 February; 6(1): 97–102).

The scientific literature states that the mode of transmission of *H. pylori* between humans is unknown. *H. pylori* has been identified in the mouths of humans in some instances, involving isolation from the dental plaque, saliva and gingival pockets. However, studies of the prevalence of oral colonization by *H. pylori* have shown variable results with most known infected persons having negative oral results (Thomas et al., 1997, supra).

In some instances an association has been observed between *H. pylori* detectable in the mouth and presence of the organism in the stomach (Mapstone, N., et al., "Identification of *Helicobacter pylori* DNA in the mouths and stomachs of patients with gastritis using PCR," J. Clin. Pathol., 1993; 46: 540–543). In some cases the strain of *H. pylori* in saliva is found to match that in the stomach (Ferguson, D., et al., "Isolation of *Helicobacter pylori* from saliva," J. Clin Microbiol., 1993 October; 31(10): 2802–2804). In lieu of oral colonization, it has been suggested that reflux of gastric contents (gastroesophageal reflux) into the oral area may be the factor accounting for occasional recovery of *H. pylori* organisms from the mouth (Madinier, I., et al., "Oral carriage of *Helicobacter pylori*: a review," J. Periodontol., 1997 January; 68(1): 2–6).

*H. pylori* has been suggested to be associated with health disorders beyond gastric inflammatory conditions (Wisniewski, R., and Peura, D., "*Helicobacter pylori*: behond peptic ulcer disease," Gastroenterologist, 1997 December; 5(4): 295–305; "The germ theory of heart disease," Newsday, Mar. 3, 1998; Markus, H., and Mendall, M.,"*Helicobacter pylori* infection: a risk factor for ischemic cerebrovascular disease and carotid atheroma," J. Neurol. Neurosurg. Psychiatry, 1998 January; 64(1): 104–107).

Detection of *H. pylori* in oral fluid samples derived from the pharynx, as an indicator of current infection status has not been described in humans until the present invention. In one study, tissue biopsies of the larynx, which lies below the pharynx and is not contacted during sampling of the pharynx, were found to contain urease activity in only a minority of subjects with chronic laryngitis (Borkowski, G., et al., "A possible role of *Helicobacter pylori* infection in the etiology of chronic laryngitis," Eur Arch Otorhinolaryngol, 1997; 254: 481–482).

Some research suggests that conditions of the pharynx or throat area may be involved in diseases of the gastrointestinal tract (Zavadiak, H., "The relationship of duodenal peptic ulcer and gastroduodenitis to a chronic staphlococcal infection," Lik Sprava, 1993 May; 5–6: 65–69; Minocha, A., et al., "Is a history of tonsillectomy associated with a decreased risk of *Helicobacter pylori* infection?", J. Clin. Gastroenterol., 1997 December; 25(4): 580–582). These studies suggest associations between changes in the lymphatic tissues and subsequent gastrointestinal disease, but not pharyngeal sampling for diagnostic purposes.

In a canine study, multiple tissue biopsies were obtained following experimental *H. pylori* infection. *H. pylori* was found in a pharynx biopsy of only one of several experimentally infected, gnotobiotic canine test subjects (Radin, M., et al., "*Helicobacter pylori* gastric infection in gnotobiotic beagle dogs," Infect. Immun., 1990 August; 58(8): 2606–2612). Canines are not naturally affected by *H. pylori* infection and these and other non-humans do not serve as a reservoir of *H. pylori*, however.

*H. pylori* produces abundant urease, more than other currently known bacteria. The high urease activity of *H. pylori* allows it to survive in an acid environment, by production of ammonia from urea and thereby signicantly elevating the pH of the environment of the organisms. The unique ability of *H. pylori* to produce abundant urease has been utilized to identify presence of the organism in solid tissue specimens placed into small test volumes containing urease substrate. In an initially acid pH environment of greater than approximately 2.5, the urease activity of *H. pylori* in a solid tissue specimen can metabolize urea to raise the pH (U.S. Pat. No. 4,923,801, Marshall and Guerrant, 1990). This and other patents cited are incorporated by reference herein. When present in significant quantities, *H. pylori* organisms have sufficient preformed urease to raise the pH in the absence of additional bacterial growth.

The urease activity of common, non-*H. pylori* bacteria is destroyed by acid environments. A relatively stronger acid environment is required to destroy the urease of *H. pylori*. Increased acidity stimulates the urease activity of *H. pylori* (Miederer, S., Grubel, P., "Profound increase of *Helicobacter pylori* urease activity in gastric antral mucosa at low pH," Dig. Dis. Sci., 1996 May; 41(5): 944–949).

The rapid urease test has a high sensitivity for detection of urease activity and is considered a reliable method for assessment of *H. pylori* infection in solid tissue specimens. One rapid form of the urease test utilizes a gel into which the tissue sample is placed (CLOtest; U.S. Pat. No. 4,748,113, Marshall, May 1998). The gel acts as a support for the tissue specimen and reagents and contains the urease substrate and pH indicator. This test requires up to 24 hours for completion. Methods of applying urea and a pH indicator to gastric mucosa during endoscopic procedures, to rapidly detect tissue colonized by *H. pylori* are also in use (Thillainayagam, A., et al., "Diagnostic efficiency of an ultrarapid endoscopy room test for *Helicobacter pylori*," Gut, 1991 May; 32(5): 467–469; Iseki, K., et al., "*Helicobacter pylori* infection in patients with early gastric cancer by the endoscopic phenol red test," Gut, 1998; 42: 20–23).

A test-strip form of the rapid urease test which provides visual results on solid tissue specimens within an hour or more at room temperature has been developed (Yousfi, M., et al., "Comparison of Agar Gel (CLOtest) or Reagent strip (PyloriTek) rapid urease tests for detection of *Helicobacter pylori* infection," *Am. J. Gastroenterol.*, 1997 June; 92(6): 997–999; Elitsur, Y., et al., "Prospective comparison of rapid urease tests (PyloriTek, CLOtest) for the diagnosis of *Helicobacter pylori* infection in symptomatic children: a pediatric multicenter study," *Am. J. Gastroenterol.*, 1998 February; 93(2): 217–219; U.S. Pat. No. 5,314,804, Boguslaski and Carrico, May 1994; U.S. Pat. No. 5,420,016, Boguslaski and Carrico, May 1995). This test strip was developed for detection of urease activity in solid tissue specimens obtained from the stomach.

2. Discussion of Prior Art

Confirmation of *H. pylori* infection is necessary to ensure appropriate therapy. Serological test methods are available which detect antibodies to *H. pylori*. These tests fail to identify a proportion of persons with gastric disease (Vaira, D., et al., "Usefulness of serology in preendoscopic screening. The Italian *Helicobacter pylori* Study Group," *Helicobacter*, 1997 July; 2 Suppl. 1: S38–S43). Also, detection of salivary antibodies to *H. pylori* has been shown to have only limited utility for diagnosis of *H. pylori* infection (Loeb, M., et al., "Evaluation of salivary antibodies to detect infection with *Helicobacter pylori*," *Can. J. Gastroenterol.*, 1997 July; 11(5): 437–440).

Ideally, body sampling methods used for identification of *H. pylori* organisms in human tissues would have ease of performance, efficiency, cost-effectiveness and adequate safety. Prior art methods of detecting *H. pylori* infection have important limitations. As discussed, one method of identification of *H. pylori* infection requires invasive tissue sampling by endoscopic procedures. Once obtained, the tissue samples are subjected to methods to detect *H. pylori*, such as involving detection of urease activity in tissue samples. Another method of diagnosis requires stool sampling coupled with laboratory analysis to detect *H. pylori* antigen in fecal matter. The drawbacks of these methods are they require specially-trained personnel and specialized equipment to perform. Also, potential health risks may be associated with invasive procedures where such are required for diagnosis.

Sampling of saliva or plaque in the oral cavity has been tested as a non-invasive means of detecting *H. pylori* infection, however it has been rejected as being unsatisfactory for diagnosis. In the prior art, there has been only a low probability of identifying *H. pylori* organisms from oral samples of persons with known gastric infection (Thomas et al., 1997, supra). Prior art methods of oral sampling for *H. pylori* have required sophisticated laboratory techniques such as identifying genetic material of the bacteria (e.g., polymerase chain reaction). See also Husson, M., et al., "Detection of *H. pylori* in saliva using a monoclonal antibody," *Int. J. Med. Microbiol. Virol., Parasitol. Infect. Dis.*, 1993 November; 279(4): 466–471.

The medical literature continues to express the opinion that the mode of transmission of *H. pylori* infection in humans is unknown and that *H. pylori* is only occasionally cultured from saliva in persons with known infection (Parsonnet, J, et al., "Fecal and oral shedding of *Helicobacter pylori* from healthy infected adults," *JAMA*, Dec. 15, 1999; 282(23): 2240–2245). The above study used induced vomiting and diarrhea to obtain gastrointestinal samples for testing. Thus the prior art teaches away from use of oral fluid sampling for diagnosis of *H. pylori* infection.

Another factor is that normally present oral bacteria can inhibit growth of *H. pylori* (Ishihara, K., et al., "Oral bacteria inhibit *Helicobacter pylori* growth," *FEMS Microbiol. Lett.*, Jul. 15, 1997; 152(2): 355–361). Thus it would be surprising that oral sampling could be used for diagnosis of *H. pylori* infection.

A method has been described for "home" detection of infection, however it requires incubation of saliva samples in selective growth media, over a period of days to enable possible detection of *H. pylori* present in such samples (U.S. Pat. No. 5,498,528, King, March 1996). Detection of urease activity as an indicator of *H. pylori* is used in gastric biopsies as a rapid test for infection, however this is based on high levels of organisms present in gastric infection. A similar approach to rapid detection of *H. pylori* using oral samples would fail, based upon prior art.

Still a further problem with oral sampling is that organisms which are native to the oral cavity have urease activity (Dibdin, G., Dawes, C., "A mathematical model of the influence of salivary urea on the pH of fasted dental plaque and on the changes occurring during a cariogenic challenge," *Caries Res.*, 1998; 32(1): 70–74). Contamination by these urease-producing organisms in the mouth can cause false-positive results when attempting to use the urease method to test tissue samples for *H. pylori* infection (Namavar, F., et al., "Presence of *Helicobacter pylori* in the oral cavity, oesophagus, stomach and faeces of patients with gastritis," *Eur. J. Clin. Microbiol. Infect. Dis.*, 1995 March; 14(3): 234–237; Marshall, B., and Surveyor, I., "Carbon-14 urea breath test for the diagnosis of *Campylobacter Pylori* Associated Gastritis," *J. Nucl. Med.*, 1988 January; 29(1): 11–16; Surveyor, I., et al., "The 14C-urea breath-test for the detection of gastric *Campylobacter pylori* infection," *Med. J. Aust.*, 1989 October; 151(8): 435–439; Marshall, B., et al., "A 20-minute breath test for *Helicobacter pylori*," *Am. J. Gastroenterol.*, 1991 April; 86(4): 438–445).

In addition, urea is normally present in saliva as a result of its production in the body (Dibdin and Dawes, 1998, supra) and is used as a substrate by the urease-producing bacteria normally present in the mouth. Therefore, even without an external urea source, oral samples can demonstrate urease activity and ammonia production. Acid pH (below 5.0) has been found to inhibit urease activity of oral bacteria including *Streptococcus salivarius* (Sissons, C., and Hancock, E., "Urease activity in *Streptococcus salivarius* at low pH," *Arch. Oral Biol.*, 1993 June; 38(6): 507–516), whereas the urease activity of *H. pylori* is active well below this pH.

Application of acidification of oral samples for selection and rapid detection of the urease activity of *H. pylori* has not been previously described. Furthermore, in light of the prior art which concludes that oral sampling is not effective for *H. pylori* diagnosis, or requires incubation of oral samples, it would not be anticipated that acidification of oral samples would have any utility in rapid *H. pylori* diagnosis. Thus it would be surprising to diagnose *H. pylori* infection in humans by selection and rapid detection of urease activity in oral samples. The latter method depends upon oral presence of viable *H. pylori* and its associated urease activity, to a degree sufficient to enable rapid and selective detection without culturing or sophisticated laboratory methods.

SUMMARY OF THE INVENTION

It is the surprising discovery of this invention that it is possible to rapidly detect the urease activity associated with *H. pylori* directly in oral liquid samples obtained in a non-invasive, non-instrumented manner and without need for sample incubation. Further, it is possible to selectively detect the urease activity associated with *H. pylori* in such samples by sample acidification.

Urease activity associated with *H. pylori* refers to urease activity in an oral liquid sample that remains intact with acidification to a pH in a range of about 5.0 to about 2.5. Selective detection of urease activity refers to detection of the urease activity associated with *H. pylori* infection, with other bacterial sources of urease not being detected.

Oral liquid samples refer to samples that are collected by the process of using water or other suitable sampling liquid to contact oral tissues, followed by retrieval of the resulting oral liquid sample for direct and rapid detection of urease activity within the sample. Rapid detection refers to test results that are provided within 1 to 2 hours. Direct detection refers to testing within the container used to retrieve and hold the sample.

Non-invasive in this instance refers to performance of diagnosis without penetration of the skin or organs. Non-instrumented in this instance refers to methods of test specimen retrieval and testing without placing one or more instruments in contact with tissue surfaces.

It is a surprising discovery of this invention that the urease activity associated with *H. pylori* infection can be detected in oral liquid samples derived from the pharynx by the process of gargling. Retrieval of oral liquid samples from the pharynx for attempted detection of urease activity associated with *H. pylori* has not been previously described. It is yet a further surprising discovery and embodiment of this invention that identification of infection by detection of urease activity in oral samples is aided by sampling of both the pharynx as well as the oral cavity or mouth.

The mouth refers to the anatomic area bounded by the cheeks, lips and arch of the palate and inclusive of the teeth and tongue. The pharynx refers to the anatomic area behind and below the mouth, commonly referred to as the throat area and separated from the mouth by the space represented by the fauces.

The process of gargling involves taking sampling liquid in the lower pharynx or throat and forcing expired breath through it while holding the head back, without intentional swallowing. The process of rinsing involves taking sampling liquid in the mouth and swishing the liquid around the tissues of the mouth, including against the gingiva and over the tongue.

Sampling of both the pharynx and mouth is discovered to be advantageous for detection of urease activity associated with *H. pylori*. Using the methods of the invention it was discovered that such activity may be detectable either in the mouth or pharynx in a human by sampling, but not necessarily in both anatomic locations at any given point in time. These anatomic locations are distinctly sampled by the processes of rinsing the mouth and gargling, respectively. Rinsing the mouth samples saliva and plaque as well as tissues in the oral cavity such as the tongue, while gargling samples tissues in the pharynx.

Furthermore, it is discovered that in a human, the location of such urease activity may change between mouth and pharynx over time, therefore effective oral sampling for infection at a point in time includes this combination of tissues. This phenomenon has not previously been described and as noted, prior art attempts at oral liquid sampling for *H. pylori* detection have been limited to the mouth. The significant limitations of the prior art of oral sampling for *H. Pylori* are thus overcome by the present invention.

Using the methods of the invention, the unanticipated observation was made that application of a urease detecting pad containing urease substrate onto a retrieved oral liquid sample of relatively large volume, e.g., 5 to 10 ml or more, also results in measurable alteration (increase) of sample pH. This pH alteration specifically occurs when the sample contains urease activity associated with *H. pylori* as demonstrated by a positive test result in a urease detecting pad in contact with the sample. A urease detecting pad refers to a pad containing urease substrate that is placed in contact with the oral liquid sample.

This observation is surprising, since in the prior art of urease detection a gastric or other solid tissue specimen directly colonized with *H. pylori* is placed into a urease indicator. Urease activity is detected by change in pH of a small area or volume, e.g., a fraction of 1 ml surrounding the tissue specimen. Further, such specimens may be incubated and retained for a prolonged period before final test result determination.

In contrast, in the present invention any *H. pylori* organisms potentially retrieved by oral sampling, without the benefit of actual colonized tissue specimens are dispersed in a considerably larger volume further diluted by the sampling liquid. Yet surprisingly, this volume of oral liquid sample is capable of demonstrating significant pH change (e.g., from below 5.0 to greater than 7.0), within 1 to 2 hours and without sample incubation, when urease activity is present in the sample. Further surprisingly, this change in oral liquid sample pH is not observed when urease substrate is mixed into such oral samples, in lieu of the invention's method of application of the urease detecting pad onto the sample for test purposes.

It is therefore an object of this invention to provide a method for rapid, specific detection of the urease activity associated with *H. pylori* infection in humans, directly in human oral liquid samples without the need for incubation.

It is a further object of this invention to provide a method for oral sampling and specific, rapid detection of the urease activity associated with *H. pylori* infection in humans, which can potentially be performed by the layperson on him/herself without professional assistance.

The foregoing and other objects, advantages and characterizing features will become apparent from the following description of certain illustrative embodiments of the invention.

The novel features which are considered characteristic for the invention are set forth in the appended claims. The invention itself, however, both as to the construction and its method of operation, together with additional objects and advantages thereof, will be best understood from the following description of the specific embodiments when read and understood in connection with the accompanying drawing. Attention is called to the fact, however, that the drawing is illustrative only, and that changes may be made in the specific construction illustrated and described within the scope of the appended claims.

BRIEF DESCRIPTION OF THE DRAWING FIGURE

Various objects, features and attendant advantages of the present invention will become more fully appreciated as the same becomes better understood when considered in conjunction with the accompanying drawing.

The FIGURE illustrates the retrieved oral liquid sample within the collection container used to retrieve and hold the sample, further demonstrating the urease detecting pad in the position of floating upon the sample. A test result can be provided from visual observation of color change in the urease detecting pad. The oral liquid sample within the collection container may also be analyzed for changes caused by reaction between urease activity present in the sample and the urease detecting pad.

DETAILED DESCRIPTION OF THE PREFERRED EMBODIMENTS

Turning now descriptively to the drawing, the FIGURE illustrates an oral sampling test method of the present invention. With regard to the reference numerals used, the following numbering is used.

10 oral liquid sample 12 collection container for retrieving and holding 10

14 urease detecting pad floating on 10 within 12

A preferred embodiment of the method involves obtaining an oral liquid sample 10 for detection of urease activity associated with *H. pylori*, by gargling or gargling and rinsing, followed by retrieval of the resulting oral liquid sample into the collection container 12 for testing.

The processes of rinsing and gargling may be performed separately with resulting retrieval of two separate oral liquid samples. This may be advantageous when it is desirable to identify the specific location of urease activity, i.e., in the mouth or pharynx. In this case, either sample may be obtained first. However, it can be further advantageous to first collect the rinse sample, which is retrieved by expectoration of the oral liquid sample into the collection containers. Rinsing and expectorating clears the mouth of saliva and other mouth components that are not desired to be present in the gargle sample, which is intended to sample the pharynx.

Alternatively, sampling of the mouth and pharnyx may be performed sequentially to provide a single oral liquid sample. In this case, it may advantageous to first perform gargling followed by mouth rinsing, followed by expectoration for retrieval of the oral liquid sample. In this method, following gargling the gargle sample is transferred within the closed mouth to the mouth area, for subsequent rinsing for sampling of mouth tissues.

Oral sampling is performed by placing a measured volume of a sampling liquid into the mouth to be used for the gargling and/or rinsing process. Measurement of the designated volume of sampling liquid and placement of same into the mouth for rinsing, or the back of the throat for gargling may be carried out by use of a hand-held implement such as a teaspoon or measuring cup.

Sampling liquid refers to a liquid with known characteristics, including pH. The sampling liquid is non-hazardous when in contact with human tissues and does not contain contamination which may affect test outcome. An example of suitable volume of sampling liquid is 5 ml or one teaspoon. Examples of sampling liquid that may be used include sterile water, saline or sterile saline. It may be desirable to utilize a sampling liquid which is similar in osmotic characteristics to physiologic fluids, e.g., sterile normal saline. Liquid of other desirable characteristics may be utilized in the sampling procedure without departing from the methods of the invention. For example, sampling liquid with characteristics helpful for the retrieval of *H. pylori* organisms or urease activity from the oral tissues may be utilized.

Rinsing is performed by swishing the sampling liquid around the mouth to contact the mouth tissues, while the mouth is closed to prevent leakage, for a period of about 5 seconds. Gargling refers to tilting the head back, allowing the sampling liquid to contact the pharynx and forcing expired air through the sampling liquid in the pharynx, also for a period of about 5 seconds. This causes the sampling liquid to come in contact with the tissues of the pharynx.

Where rinsing is performed alone or follows gargling in sequence, the resulting oral liquid sample is retrieved by expectorating (spitting) into the collection container. Ideally as much of the sample as possible is retrieved.

Where gargling is performed alone, the resulting oral liquid sample is retrieved by tilting the head forward and opening the mouth, allowing the sample to fall by force of gravity from the mouth into the collection container, without expectorating. This practice helps to limit possible contamination of the gargle sample with saliva and other components of the mouth.

Whenever rinsing and gargling are performed sequentially to provide a single oral liquid sample, irrespective of the order in which they are performed retrieval of sample may be performed by expectoration, as the sample is intended to contain saliva and other mouth components.

Ideally, as much oral liquid sample as reasonably possible is retrieved to ensure detection of urease activity when such is present. A small amount of the sampling liquid may be retained in the mouth without hazard and without disadvantage to the testing.

The collection container 12 is particularly suited to the method of retrieving an oral liquid sample through the open mouth; placement of the urease detecting pad 14 onto the retrieved oral liquid sample 10 within the collection container; and visual observation of the urease detecting pad for color change indicative of urease activity. The collection container is made of solid material (e.g., glass or plastic) and may be cup-shaped to be held in the hand during oral liquid sample retrieval from the mouth, and to subsequently lie on a flat surface in the upright position for placement of the urease detecting pad onto the sample and observation for color change.

The open end of the collection container is of a sufficient diameter for retrieval of sample from the mouth as the collection container is held in proximity to the mouth; and for visual observation of the urease detecting pad floating upon the sample. The open and closed ends are of sufficient diameters to allow for the urease detecting pad to float upon the surface of the sample and for the closed end to be stable when lying on a flat surface. The container need not be translucent, as the open end allows for visual observation of the urease detecting pad for evidence of color change.

The collection container has a volume sufficient to fully hold an oral liquid sample, where the sample has a vertical dimension in the collection container. The volume of the retrieved oral liquid sample is in the general range of about 5 to about 10 ml, when 5 ml of sampling liquid is used to obtain the sample by rinsing and/or gargling. The volume of retrieved oral liquid sample varies with individual differences, such as the amount of saliva present in the mouth.

Saliva present in the oral liquid sample can contain preformed ammonia as a result of the reaction between salivary urea and the urease activity of non-*H. pylori* organisms normally present in the mouth. Also, in its usual state the urease activity of these non-*H. pylori* organisms may react with a urease substrate present on the urease detecting pad.

Acid pretreatment (acidification) of the oral liquid sample is performed to inhibit or eliminate these saliva effects unrelated to *H. pylori*, including preformed ammonia and urease activity of non-*H. pylori* bacteria present in the oral liquid sample. Acidification is performed prior to testing of urease activity and may be accomplished by addition of an acidifying agent, such as acidifying solution to the oral liquid sample within the collection container, sufficient to reduce the pH to about 5.0 but above about 2.5. In this range the urease activity associated with *H. pylori* remains active, while other sources of urease activity are not active.

Detection of urease activity in the retrieved oral liquid sample is performed by placement of the urease detecting pad 14 in a floating position on the sample, following sample acidification. The urease detecting pad can provide a visually observable color change in response to the presence of ammonia vapor. The ammonia vapor is created by reaction between a urease substrate, such as urea present in the urease detecting pad and urease activity present in the oral liquid sample.

The urease detecting pad consists of multiple elements connected to form a single structure. In conjunction with urease activity present in the oral liquid sample, these elements perform the functions necessary to cause formation and detection of ammonia vapor. The urease detecting pad is formed of lightweight material such that it will remain in a floating position when placed upon the oral liquid sample.

In its unused state, the urease detecting pad contains the urease substrate in dried form, located on the urease substrate element. To bring the urease substrate in contact with the oral liquid sample and to become activated by contact with the aqueous environment of the sample, the urease substrate element of the urease detecting pad is an absorbent, water-insoluble material impregnated with the urease substrate. This material may be a matrix of woven or unwoven fabric, cellulosic paper or other hydrophilic material. Urea concentrations of 5 mM or higher in the urease substrate element are suitable for sensitive detection of urease activity in the oral liquid sample.

To provide for detection by the urease detecting pad of ammonia vapor created by reaction between the urease substrate and urease activity present in the oral liquid sample, the ammonia vapor must be transported from the aqueous environment of the urease substrate element and be brought into contact with a pH indicator element of the urease detecting pad. The pH indicator is in a dry state and undergoes a color change reflecting the increase in pH upon contact with ammonia vapor. A hydrophobic diffusion element of the urease detecting pad lies between, and is contiguous with the urease substrate element and the pH indicator element.

The hydrophobic diffusion element allows ammonia vapor to pass but is impermeable to the oral liquid sample, thereby allowing ammonia vapor to effectively be transported to contact the pH indicator element. The hydrophobic diffusion element, typically a membrane must be thin to expedite diffusion of the ammonia vapor. Commercially available membrane materials for this purpose range from 50 to 250 micrometers in thickness, with pore diameters ranging from 0.05 to 10 micrometers. Pore diameters in the higher end of this range are preferable to reduce resistance to diffusion. Suitable membrane material includes various polymers, such as polyvinyl chloride.

The test result of the urease detecting pad is provided by observation for presence or absence of color change of the pH indicator element. The color of the pH indicator element is visualized by observing the urease detecting pad within the collection container. pH indicators in common use change from one distinct color in the acid form to another distinct color upon deprotonation by ammonia. Visualization of the test result is aided by change of the pH indicator from a relatively weak color in the acid form to a strong color in the basic form.

In order to provide a visually detectable color change, the pH indicator should have a pKa in the range of about 2.0 to about 6.0. Bromophenol Blue in dry form may be utilized as, the pH indicator of the pH indicator element. This pH indicator is a pale yellow in the acid form and converts to a blue color in the basic form, upon contact with ammonia vapor.

The elements of the urease detecting pad are aligned vertically to form one structure that is sealed at its edges, with the urease substrate element forming the bottom of the structure in contact with the oral liquid sample. The pH indicator element is not contacted by the sample. In the absence of ammonia vapor contacting the pH indicator element, the pH indicator does not undergo a color change.

The pH indicator element ideally is thin to allow for visualization of color change by observation of the urease detecting pad, which presents the side of the pH indicator element away from the hydrophobic diffusion membrane. Microporous membranes ate useful for this purpose. The pH indicator may be impregnated onto the microporous membrane or present on pH indicator paper directly contiguous with the microporous membrane, the combination of pH indicator paper and microporous membrane forming the pH indicator element. The microporous membrane may be of hydrophobic or hydrophilic. material.

In order for the ammonia vapor to contact the pH indicator element and cause color change, it is necessary that the ammonia vapor be retained within the urease detecting pad such that it will not otherwise diffuse into the surrounding air. This is accomplished by sealing the full perimeter and the top surface of the urease detecting pad with a light-transmitting substance, such that the top surface of the urease detecting pad remains visible. This seal does not include the bottom surface of the urease substrate element, as the urease substrate must contact the oral liquid sample. Ammonia vapor thus created passes through the hydrophobic diffusion element to subsequently be retained for contact with the pH indicator element.

The urease detecting pad may have a round disk-shaped configuration and is of a diameter smaller than the open end of the collection container. The disk shape of the urease detecting pad corresponds with the typically round or cup-type shape of the collection container, furthermore the shape of the urease detecting pad can be such that it facilitates the incorporation of one or more test monitor or control areas into it. For example, the detecting area and one or more monitor areas (negative, positive or both) can occupy concentric areas of the urease detecting pad.

As an example, a negative control may be incorporated into the urease detecting pad for detection of residual saliva effects in the oral liquid sample capable of causing false-positive results. While acidification of the oral liquid sample is performed to eliminate or inhibit such effects, residual saliva effects following acidification might affect test results. Preformed ammonia deriving from the saliva can cause a positive result in the urease detecting pad, even though urease activity may be absent from the oral liquid sample. The negative control region of the urease detecting pad can lack urease substrate, therefore a positive result in the negative control region would indicate presence of residual saliva effects in the oral liquid sample unrelated to urease activity associated with *H. pylori*.

The urease detecting pad provides a rapid result for presence of urease activity in the oral liquid sample. The oral liquid sample is kept at room temperature, without incubation and provides a test result typically within 1 to 2 hours of placement of the urease detecting pad on the sample.

In a further embodiment of the method, the pH of the oral liquid sample is monitored during the test procedure. From a starting pH of about 5.0 or lower (after acidification), the pH of the oral liquid sample typically increases to a pH above 7.0 when urease activity is present in the oral liquid sample, as can be indicated by a positive result in the urease detecting pad.

Oral liquid sample pH may be identified by various means, such as by addition of pH indicator to the sample. The pH indicator may be added to the oral liquid sample following acidification and prior to placement of the urease detecting pad, in order to record initial sample pH and post-test pH.

Bromothymol Blue solution can be used as the pH indicator in this method and provides a colorimetric indicator of oral liquid sample pH, upon addition to the sample. Bromothymol Blue pH indicator changes from light yellow color in the initial acid sample, to blue color when the sample pH rises to 7.0 or higher.

Measurement of the pH of the oral liquid sample following placement of the urease detecting pad on the sample is an additional, or alternative means of detecting urease activity of *H. pylori* in the sample. The change in oral liquid sample pH could potentially be used as the primary or sole indicator of urease activity in the sample, for example when the urease detecting pad is applied to the sample but lacks an operative pH indicator element, or is not constructed to contain a pH indicator element.

The pH change of the oral liquid sample results from the diffusion of ammonia vapor into the oral liquid sample, as a result of the reaction between the urease activity in the oral liquid sample and the urease substrate of the urease detecting pad. A similar effect is not observed when urease substrate is placed into the oral liquid sample containing urease activity, where the urease substrate is not an element of a urease detecting pad. The urease detecting pad appears to provide a stable reaction surface between the urease activity of the oral liquid sample and the urease substrate element to result in ammonia vapor diffusion into the sample.

While the invention specifically relates to the detection of urease activity in oral liquid samples, the test procedures may potentially be applied to detection of a range of chemical activities such as may be associated with organisms present in oral liquid samples. The types of chemical activities which can be detected in this manner are merely limited by the availability of rapid assays which can be performed within the collection container, without need for incubation.

In all cases, the detecting pad contacts the retrieved oral liquid sample in the collecting container, thereby causing the reagent or reagents of the detecting pad to undergo reaction with the oral liquid sample and provide evidence of presence or absence of the specified chemical activity as a rapid test, i.e., provision of test results within minutes to hours, without the need for sample incubation.

EXAMPLES

Testing was performed using the methods of the invention to evaluate urease activity detection in retrieved oral liquid samples. Initially, the mouth was rinsed out with tap water prior to sampling periods to remove gross contaminants including food particles.

An oral liquid sample of the gargle sample type was obtained by having the human test subject place 5 ml of sampling liquid (water) using a teaspoon into the back of the throat. This was immediately followed by gargling for a period of 5 seconds, without swallowing and then tilting the head forward, allowing the resulting oral liquid sample to fall from the open mouth into the collection container without expectoration. No sampling by rinsing the mouth with the sampling liquid was performed in this test. The volume of the retrieved oral liquid sample was approximately 5 ml.

Subsequently, acidifying solution was then added to acidify the sample to between pH 5.0 and pH 2.5. Bromothymol Blue pH indicator solution was then added to the sample, resulting in a yellow-green color to the sample and consistent with the acidification of the sample. The sample was maintained at room temperature. A urease detecting pad containing urease substrate and a pH indicator element was then placed onto the oral liquid sample, with the urease substrate element in contact with the sample. The urease detecting pad remained floating on the oral liquid sample.

Color change of the pH indicator element of the urease detecting pad was observed, from initial pale yellow to blue, beginning within 1 hour of urease detecting pad placement and further increasing to maximum between 1 and 2 hours of placement. Concurrently during this time period color change of the oral liquid sample was observed, from yellow-green to blue. The color change of the pH indicator element indicated the presence of urease activity in the oral liquid sample. The color change of the oral liquid sample, indicating significant increase in pH of the oral liquid sample upon which the urease detecting pad had been placed, to a pH of about 7.0 or more basic, further confirmed presence of this urease activity.

In the same human subject, a second oral liquid sample was next obtained by having the subject place 5 ml of sampling liquid (water) using a teaspoon into the mouth, followed by rinsing for 5 seconds, without gargling and then expectoratng into the collection container. The volume of the retrieved oral liquid sample was approximately 10 ml., indicating the contribution of saliva present in the mouth to the retrieved oral liquid sample. Procedures were then performed as described for the gargle sample, including sample acidification. By 2 hours, no color change was observed in the urease detecting pad or in the oral liquid sample to which pH indicator solution had been added, indicating absence of urease activity in the sample.

On a subsequent day, the same human subject repeated gargle and rinse sample preparation and testing, confirming positive results for the gargle sample and negative results for the rinse sample. This testing demonstrated the ability to detect urease activity in oral liquid samples from the pharynx and that rinse and gargle samples can provide different results using this test method.

Following a prolonged lapse of time, the same human subject performed separate gargle and rinse sampling and testing as on the previous occasion. This time, the gargle sample provided negative results, while the rinse sample was positive for urease activity. On a subsequent day, the procedures were repeated, with confirmation of the negative gargle and positive rinse samples. This testing demonstrated the ability of this urease activity to change location between the pharynx and mouth over time, as represented by rinse and gargle samples.

Then on still a subsequent day, the same human subject performed sequential gargling and rinsing to form one oral liquid sample, following initial placing of 5 ml of sampling water into the back of the throat. This combined gargle/rinse oral liquid sample demonstrated positive results, consistent with the currently positive rinse sample for this subject. This testing demonstrated the use of combined rinsing/gargling to sample both the mouth and pharynx, to obtain an oral liquid sample for detection of urease activity.

While the invention has been illustrated and described as embodied in a method for oral sampling for identification of urease activity associated with *H. pylori*, it is not intended to be limited to the details shown, since it will be understood that various omissions, modifications, substitutions and changes in the forms and details of the formulation illustrated and in its operation can be made by those skilled in the art without departing in any way from the spirit and scope of the present invention.

Without further analysis, the foregoing will so fully reveal the gist of the present invention that others can, by applying current knowledge, readily adapt it for various applications without omitting features that, from the standpoint of prior art, fairly constitute essential characteristics of this invention.

What is claimed as new and desired to be protected by Letters Patent is set forth in the appended claims:

1. A method for detecting *Helicobacter pylori* infection in a human, comprising:
   (a) gargling with a designated volume of a sampling liquid, without expectorating, to provide an oral liquid sample,
   (b) tilting the head forward and opening the mouth, such that said oral liquid sample enters a collection container,
   (c) acidifying said oral liquid sample in said collection container such that the pH of said oral liquid sample is below about 5.0 but above about 2.5,
   (d) contacting said oral liquid sample in said collection container with a urease detecting pad containing urease substrate,
   (e) observing said urease detecting pad for a color change or lack of color change, and
   (f) correlating said color change or lack of color change with presence or absence of *Helicobacter Pylori* infection in said human,
whereby said detecting of *Helicobacter Pylori* infection is performed without incubating of said oral liquid sample.

2. The method of claim 1, further including
   (a) measuring the pH of said oral liquid sample in said collection container before contacting said oral liquid sample with said urease detecting pad,
   (b) measuring the pH of said oral liquid sample in said collection container after contacting said oral liquid sample with said urease detecting pad, and
   (c) correlating a change in pH of said oral liquid sample with presence or absence of *Helicobacter Pylori* infection in said human,
whereby an increase in pH correlating with presence of *Helicobacter Pylori* infection, requires said contacting of said oral liquid sample with said urease detecting pad.

3. A method for detecting *Helicobacter Pylori* infection in a human, comprising:
   (a) gargling and then rinsing with a designated volume of a sampling liquid to provide an oral liquid sample,
   (b) expectorating said oral liquid sample into a collection container,
   (c) acidifying said oral liquid sample in said collection container such that the pH of said oral liquid sample is below about 5.0 but above about 2.5,
   (d) contacting said oral liquid sample in said collection container with a urease detecting pad containing urease substrate,
   (e) observing said urease detecting pad for a color change or lack of color change, and
   (f) correlating said color change or lack of color change with presence or absence of *Helicobacter Pylori* infection in said human,
whereby the pharynx and mouth are sampled by a single oral liquid sample, and
whereby said detecting of *Helicobacter Pylori* infection is performed without incubating of said oral liquid sample.

4. The method of claim 3, further including
   (a) measuring the pH of said oral liquid sample in said collection container before contacting said oral liquid sample with said urease detecting pad,
   (b) measuring the pH of said oral liquid sample in said collection container after contacting said oral liquid sample with said urease detecting pad, and
   (c) correlating a change in pH of said oral liquid sample with presence or absence of *Helicobacter Pylori* infection in said human,
whereby an increase in pH correlating with presence of *Helicobacter Pylori* infection, requires said contacting of said oral liquid sample with said urease detecting pad.

5. A method for detecting *Helicobacter Pylori* infection in a human, comprising:
   (a) rinsing with a first designated volume of a sampling liquid to provide a first oral liquid sample,
   (b) expectorating said first oral liquid sample into a first collection container,
   (c) gargling with a second designated volume of a sampling liquid, without expectorating, to provide a second oral liquid sample,
   (d) tilting the head forward and opening the mouth, such that said second oral liquid sample enters a second collection container,
   (e) acidifying said first and said second oral liquid samples in said first and said second collection containers-such that the pH of said first and said second oral liquid samples is below about 5.0 but above about 2.5,
   (f) contacting said first oral liquid sample in said first collection container with a first urease detecting pad containing urease substrate,
   (g) contacting said second oral liquid sample in said second collection container with a second urease detecting pad containing urease substrate,
   (h) observing said first and said second urease detecting pads for color change or lack of color change, and
   (i) correlating said color change or lack of color change of said first and said second urease detecting pads with presence or absence of *Helicobacter Pylori* infection in said human,
whereby the mouth and pharynx are sampled separately, and whereby said detecting of *Helicobacter Pylori* infection is performed without incubating of said first and said second oral liquid samples.

6. The method of claim 5, further including
   (a) measuring the pH of said first and said second oral liquid samples in said first and said second collection containers before contacting said oral liquid samples with said urease detecting pads,
   (b) measuring the pH of said first and said second oral liquid samples in said collection containers after contacting said oral liquid samples with said urease detecting pads, and (c) correlating a change in pH of said first and said second oral liquid samples with presence or absence of *Helicobacter Pylori* infection in said human, whereby an increase in pH correlating with presence of *Helicobacter Pylori* infection, requires said contacting of said oral liquid samples with said urease detecting pads.

* * * * *